(12) United States Patent
Cheng et al.

(10) Patent No.: US 11,229,535 B2
(45) Date of Patent: Jan. 25, 2022

(54) SHOCK-ABSORBING TWISTING STRUCTURE

(71) Applicant: Ken Dall Enterprise Co., Ltd., New Taipei (TW)

(72) Inventors: Chia-Pao Cheng, New Taipei (TW); Chih-Hsuan Liang, New Taipei (TW); Hsiang-Ming Wu, New Taipei (TW)

(73) Assignee: KEN DALL ENTERPRISE CO., LTD., New Taipei (TW)

( * ) Notice: Subject to any disclaimer, the term of this patent is extended or adjusted under 35 U.S.C. 154(b) by 143 days.

(21) Appl. No.: 16/827,717

(22) Filed: Mar. 24, 2020

(65) Prior Publication Data
US 2021/0298923 A1 Sep. 30, 2021

(51) Int. Cl.
| | | |
|---|---|---|
| A61F 2/62 | (2006.01) | |
| A61F 2/74 | (2006.01) | |
| A61F 2/64 | (2006.01) | |
| F16F 15/123 | (2006.01) | |
| F16F 15/16 | (2006.01) | |
| A61F 2/68 | (2006.01) | |
| F16F 15/121 | (2006.01) | |
| A61F 2/50 | (2006.01) | |
| A61F 2/60 | (2006.01) | |

(52) U.S. Cl.
CPC .......... *A61F 2/64* (2013.01); *A61F 2/68* (2013.01); *F16F 15/1213* (2013.01); *F16F 15/1217* (2013.01); *F16F 15/161* (2013.01); *A61F 2/748* (2021.08); *A61F 2002/5003* (2013.01); *A61F 2002/503* (2013.01); *A61F 2002/5006* (2013.01); *A61F 2002/5007* (2013.01); *A61F 2002/5033* (2013.01); *A61F 2002/5043* (2013.01); *A61F 2002/5075* (2013.01); *A61F 2002/607* (2013.01)

(58) Field of Classification Search
CPC .............. A61F 2/602; A61F 2002/5003; A61F 2002/5006; A61F 2002/5033; F16F 15/1217; F16F 15/1338
USPC .......................................................... 623/35
See application file for complete search history.

(56) References Cited

FOREIGN PATENT DOCUMENTS

KR 2001-0055392 A * 7/2001 ............... A61F 2/66

\* cited by examiner

*Primary Examiner* — David H Willse
(74) *Attorney, Agent, or Firm* — Leong C. Lei (57) ABSTRACT

A shock-absorbing twisting structure includes a first seat and a second seat. The first seat includes an elastic member. A stop member is arranged at one side of the first seat. The second seat is formed with a receiving chamber that is fit over the first seat, such that the elastic member is set in elastic engagement with and is supported between the first seat and the second seat. A main axle penetrates through the second seat and is received in the first seat to set the second seat in a rotatable condition. An elastic unit is arranged at each of two sides of the receiving chamber and the stop member.

6 Claims, 11 Drawing Sheets

SHOCK-ABSORBING TWISTING STRUCTURE

TECHNICAL FIELD OF THE INVENTION

The present invention relates generally to a shock-absorbing twisting structure, and more particularly to a structure that reduces impact in an up-down direction and also reduces twisting impact and enables easy adjustment of a twisting angle to enhance security and comfortableness of walking for a prosthesis user.

DESCRIPTION OF THE PRIOR ART

A prosthesis is generally an artificial limb that is used to functionally replace a damaged limb or to aesthetically modify the outside appearance of a damaged limb. For an artificial limb, in addition to the structure of knee joint, a shock-absorbing twisting structure is also a key issue of design, because in addition to impact in an up-down direction generated during walking and moving on different types of roads, there is also twisting impact generated in a direction (such as a radial direction) other than the up-down direction. Such impact must be reduced with a shock-absorbing twisting structure in order to maintain dynamic balance for an artificial limb to take the place of a natural limb for the purposes of supporting and walking.

U.S. Pat. No. 6,645,253 provides a vacuum pump and a shock absorber for an artificial limb, of which a structure is made primarily for cushioning and shock absorption in an up-down direction; however, no twisting structure is provided to handle twisting impact that is generated in a direction other than the up-down direction due to variations of terrain and road condition during walking. Apparently, the known patent is incapable of reducing and cushioning twisting impact.

SUMMARY OF THE INVENTION

An objective of the present invention is to provide a shock-absorbing twisting structure that reduces impact in an up-down direction and also reduces twisting impact.

To achieve the above objective, the present invention provides a structure that comprises a first seat and a second seat, wherein the first seat comprises an elastic member, a stop member being arranged at one side of the first seat; and the second seat is formed with a receiving chamber that is fit over the first seat, such that the elastic member is set in elastic engagement with and is supported between the first seat and the second seat, a main axle penetrating through the second seat and received in the first seat to set the second seat in a rotatable condition, an elastic unit being arranged at each of two sides of the receiving chamber and the stop member.

As such, during walking, the elastic member is acted upon by a force and is thus compressed, and through an effect of elastic regulation achieved with the elastic property of the elastic member, an effect of cushioning and shock absorbing in an up-down direction is provided. The first seat and the second seat, upon acted on by a force, may twist and rotate relative to each other and through an effect of elastic twisting resulting from elastic regulation achieved with the elastic unit, impact in an up-down direction caused by walking can be reduced and twisting impact acting in a direction other than the up-down direction resulting from variations of terrain of walking and road condition can also be reduced.

Further, a user is allowed to adjust an elastic pushing force provided by the elastic unit in order to make adjustment of a twisting angle between the first seat and the second seat.

A detailed description will be provided below with reference to an embodiment and the attached drawings.

DETAILED DESCRIPTION OF THE PREFERRED EMBODIMENT

Referring to FIGS. 1-5, the present invention provides a structure that comprises a first seat 10 and a second seat 20. Details are provided below:

The first seat 10 comprises an elastic member 11. A stop member 12 is arranged at one side of the first seat 10.

The second seat 20 is formed with a receiving chamber 21 that is fit over the first seat 10, such that the elastic member 11 is set in elastic engagement with and is supported between the first seat 10 and the second seat 20. A main axle 22 penetrates through the second seat 20 and is received in the first seat 10 to set the second seat 20 in a rotatable condition. An elastic unit 24 is arranged at each of two sides of the receiving chamber 21 and the stop member 12.

In an embodiment, the second seat 20 is provided on an upper side thereof with a pivot axle 25. The pivot axle 25 is pivotally connected with an arc plate 31 of a knee joint 30. The main axle 22 is provided thereon with an elastic element 26. The elastic element 26 extends through a bottom portion of the knee joint 30 and functions to assist the elastic member 11 for regulation and adjustment of elastic property.

As such, the second seat 20 is coupled to the knee joint 30 at an underside thereof and the first seat 10 is coupled to a prosthesis shank.

In an embodiment, the elastic unit 24 comprises an adjusting member 241, an elastic body 242, and a pushing portion 243. The adjusting member 241 is screwed to and attached to the receiving chamber 21. The elastic body 242 is disposed between the adjusting member 241 and the pushing portion 243. A transmitting body 23 is arranged between the pushing portion 243 and the stop member 12 to allow the pushing portion 243 to contact and elastically push the transmitting body 23.

As such, a user may make adjustment by moving and thus changing a depth of the adjusting member 241 extending into the receiving chamber 21 in order to compress or release the elastic body 242, so that a magnitude of a spring force that the pushing portion 243 is applied to push the transmitting body 23 is properly regulated and adjusted to enable adjustment of a twisting angle between the first seat 10 and the second seat 20.

The above provides a description of each of the components/parts of the present invention, and in the following, a description of examples of use, features, and efficacies of the present invention will be provided.

Referring to FIGS. 6-9, when the present invention put into use for walking, the first seat 10 and the second seat 20, upon acted upon by a force, twist and rotate relative to each other, meaning the second seat 20 rotates in a predetermined direction or an opposite direction relative to the first seat 10. The stop member 12 does not move and contact with one side of the transmitting body 23 for stopping, so that the transmitting body 23 pushes, at one side thereof, against the pushing portion 243 to thereby compress the elastic body 242 to generate a spring force. Through an effect of elastic twisting resulting from elastic regulation caused by the elastic property of the elastic body 242, an impact force acting in an up-down direction generated during walking can be reduced, and a twisting impact force, which acts in a direction other than or different from the up-down direction, resulting from variations of the terrain and road conditions encountered during walking can also be reduced.

Figure 1:
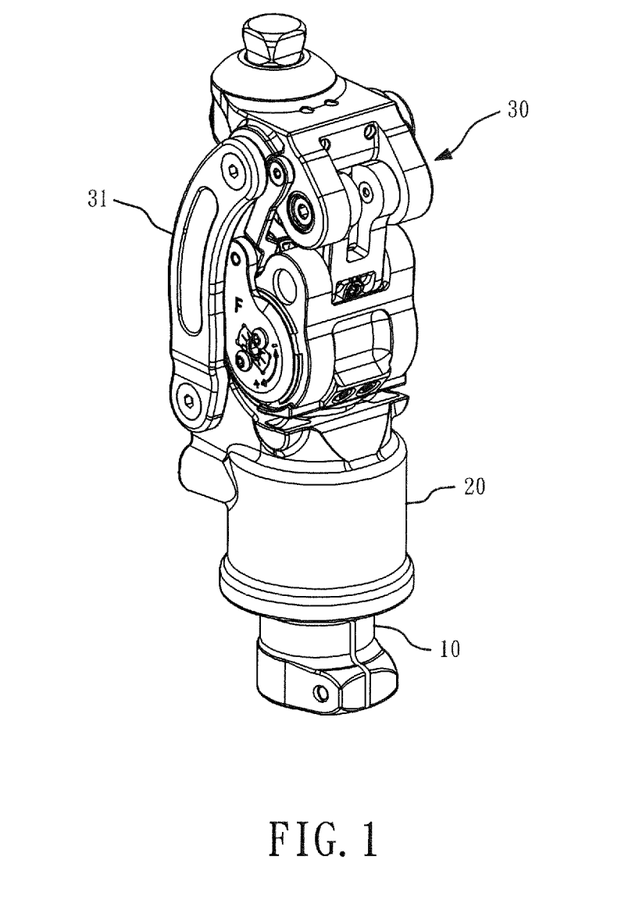
FIG. 1 is a perspective view showing the present invention.
Figure 2:
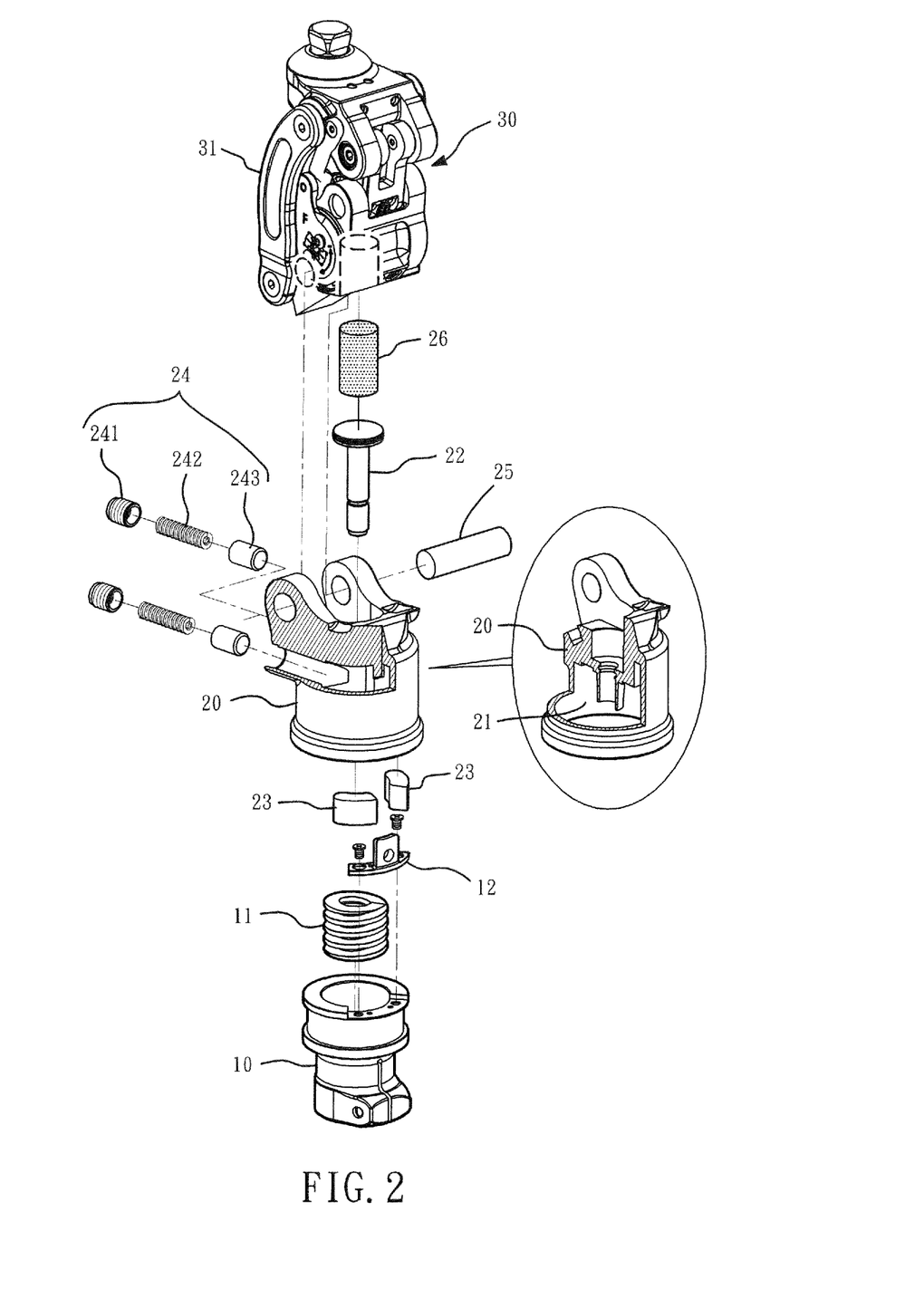
FIG. 2 is a perspective view, in an exploded form, showing the present invention.
Figure 3:
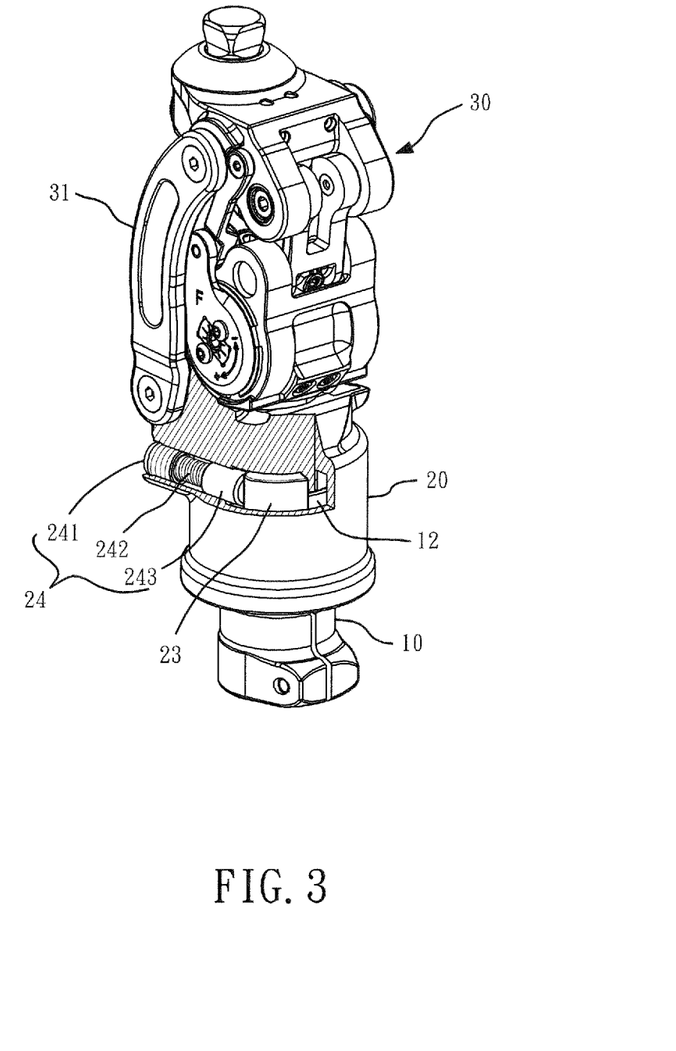
FIG. 3 is a perspective view, partly broken, showing the present invention.
Figure 4:
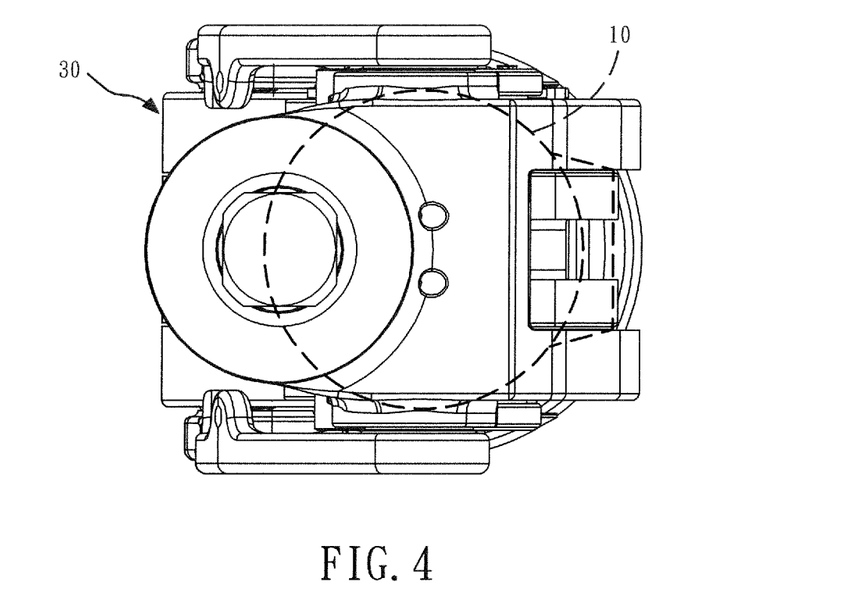
FIG. 4 is a top plan view showing the present invention.
Figure 5:
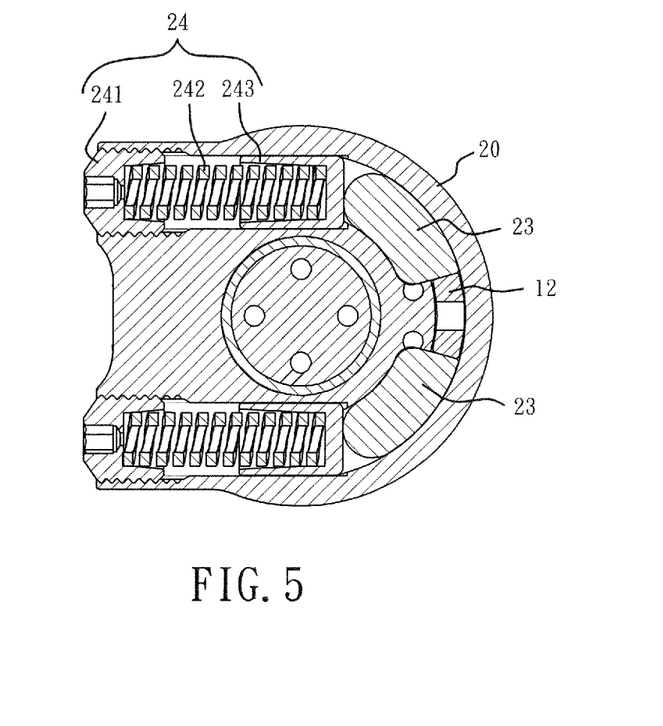
FIG. 5 is a cross-sectional view of FIG. 4.
Figure 6:
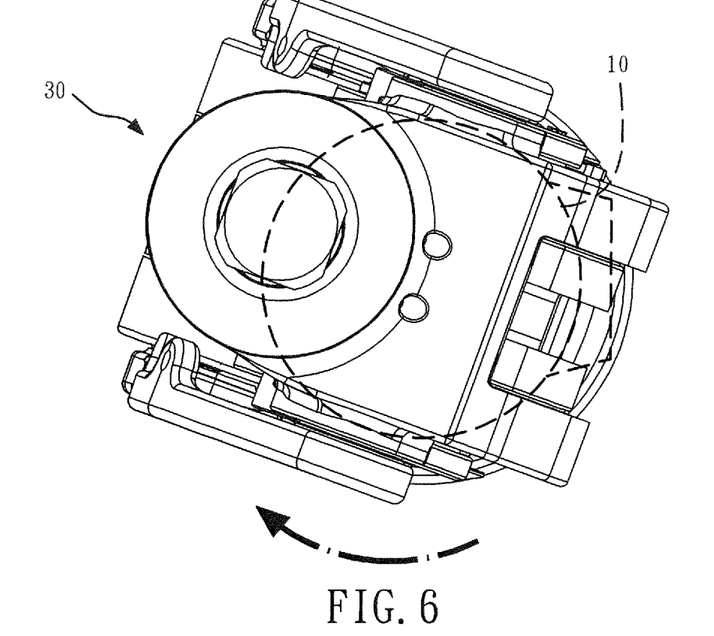
FIGS. 6-9 are schematic views illustrating an example of use of the present invention to demonstrate an effect of elastic torsion.
Figure 7:
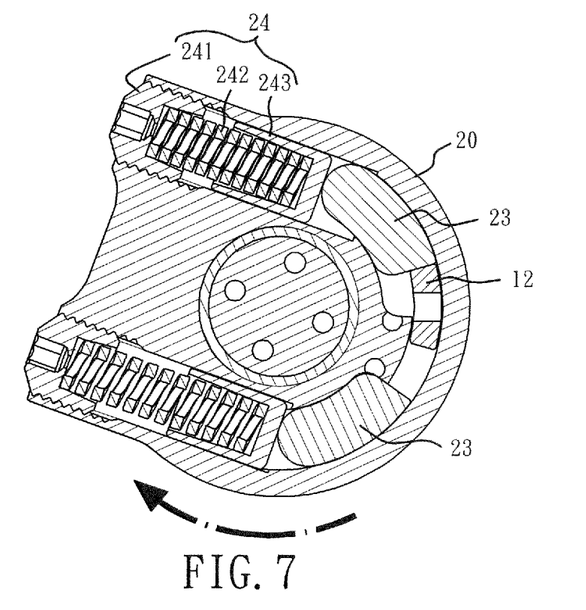
Figure 8:
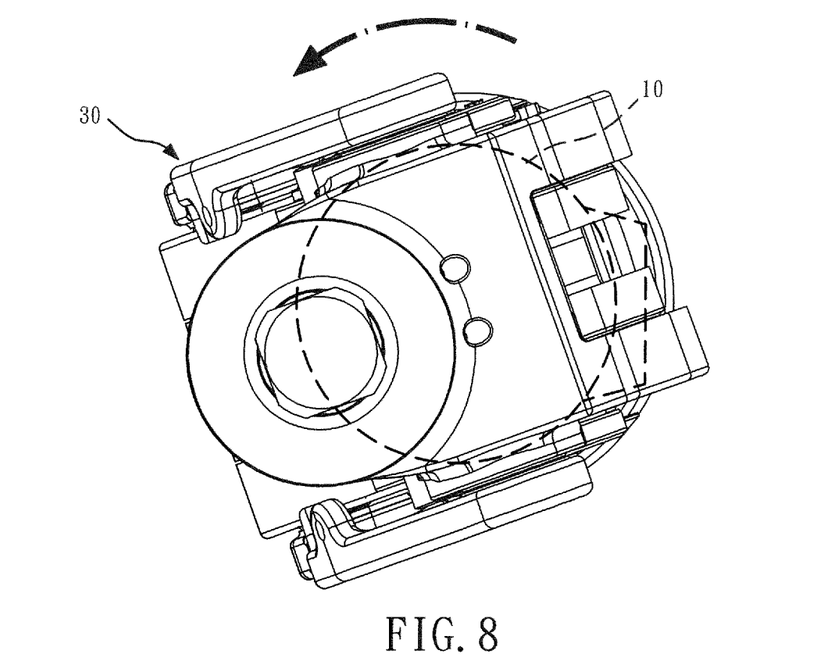
Figure 9:
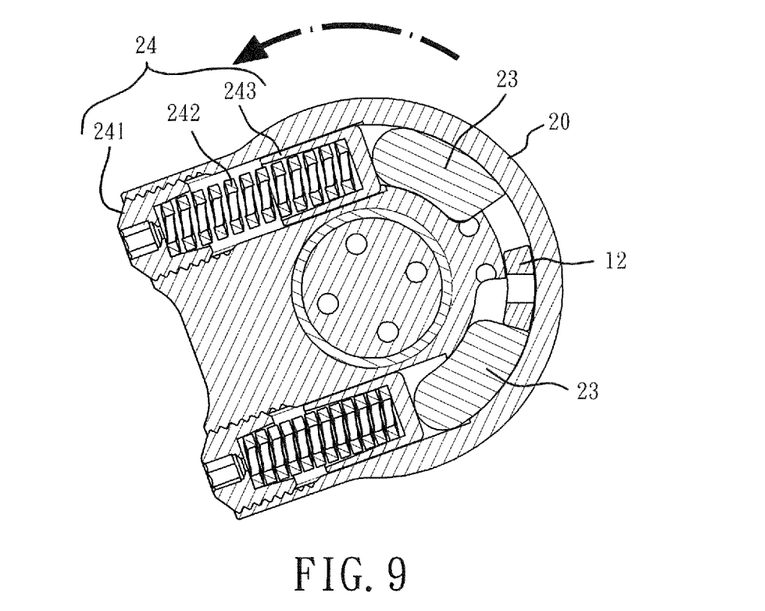
Figure 10:
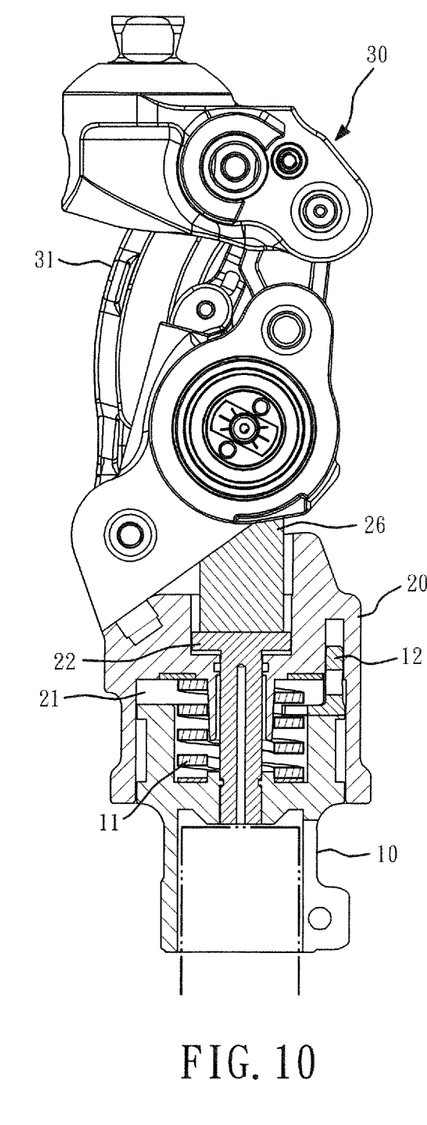
FIGS. 10 and 11 are schematic views illustrating an example of use of the present invention to demonstrate an effect of cushioning and shock absorbing in an up-down direction.
Figure 11:
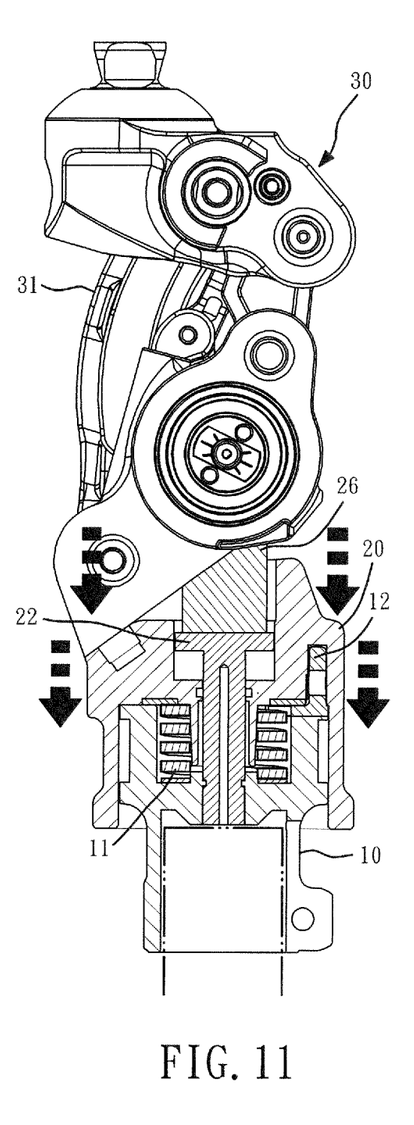

Referring to FIGS. 10 and 11, when the present invention is put into operation during walking, the second seat 20 is moved downward and applying a pressing force and the elastic member 11 is pressed by the force, wherein the effect of elastic regulation provided by the elastic member 11 achieves an effect of cushioning and shock absorbing in the up-down direction.

Figure 12:
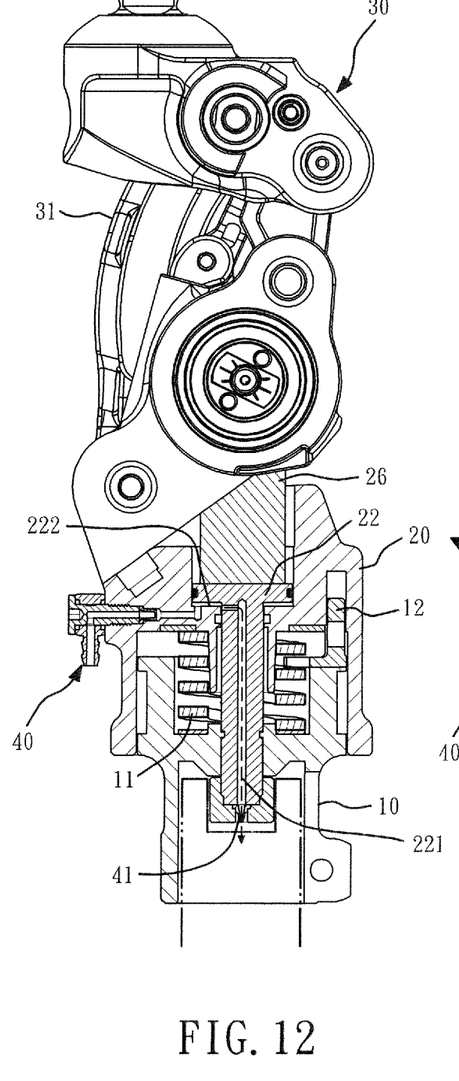
FIGS. 12 and 13 are schematic views illustrating an example of use of the present invention to demonstrate an effect of discharge and intake of air.
Figure 13:
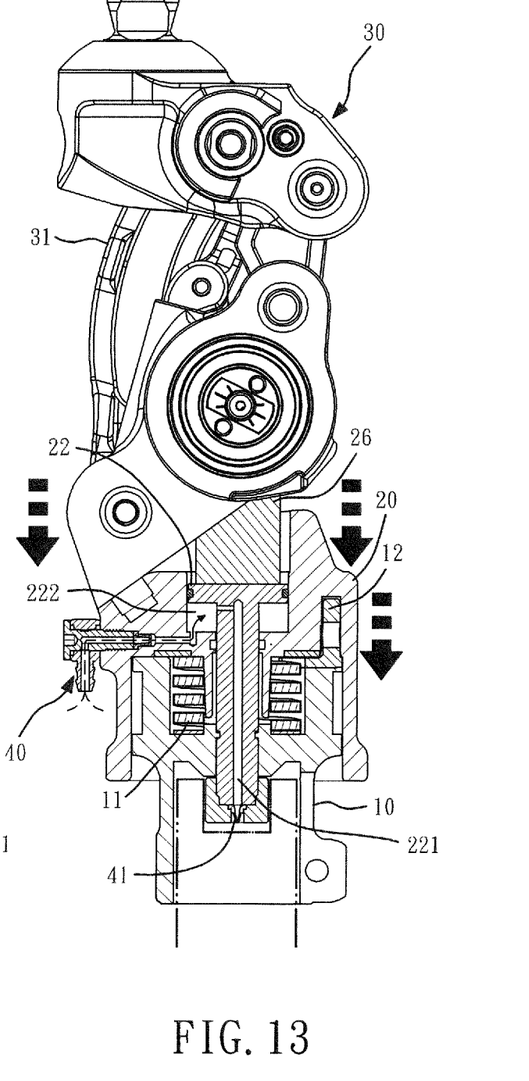

Referring to FIGS. 12 and 13, in an embodiment, the main axle 22 comprises an air passage 221 formed therein. The air passage 221 has an end in communication with the outside of the first seat 10, and the air passage 221 has an opposite end in communication with an air compartment 222 formed and delimited by an outside surface on an upper side of the main axle 22 and an inside surface of the second seat 20. The second seat 20 is provided with a one-way valve 40, and the one-way valve 40 allows external gas or air to flow, in one single direction, into the air compartment 222. The air passage 221 is connected, at one end thereof, to a reverse stop valve 41, and the reverse stop valve 41 allows gas or air to flow from the air passage 221, in one single direction, to the outside of the first seat 10.

As such, when the second seat 20 moves upward, the air compartment 222 is compressed and gas or air discharges through the air passage 221 and the reverse stop valve 41.

Oppositely, when the second seat 20 moves downward, an effect of intake is caused and external gas or air is drawn through the one-way valve 40 into the air compartment 222. Through repeating the previously discussed operation, movement of the second seat 20 in the up-down direction is stabilized and uncomfortable shock can be cushioned and improved.

Figure 14:
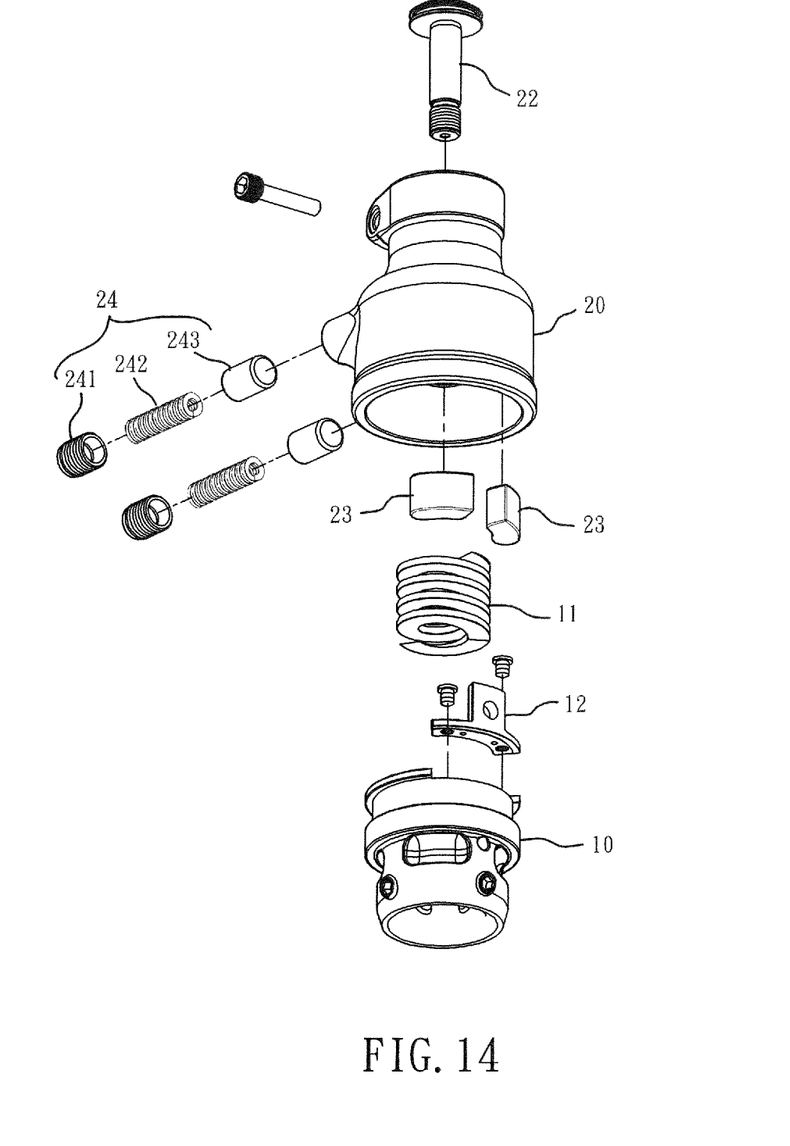
FIG. 14 is an exploded view showing another structure according to the present invention.
Figure 15:
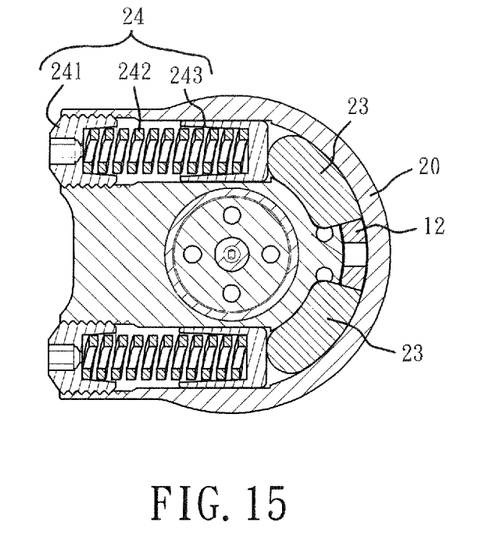
FIG. 15 is a cross-sectional view, taken in a horizontal direction, showing said another structure according to the present invention.
Figure 16:
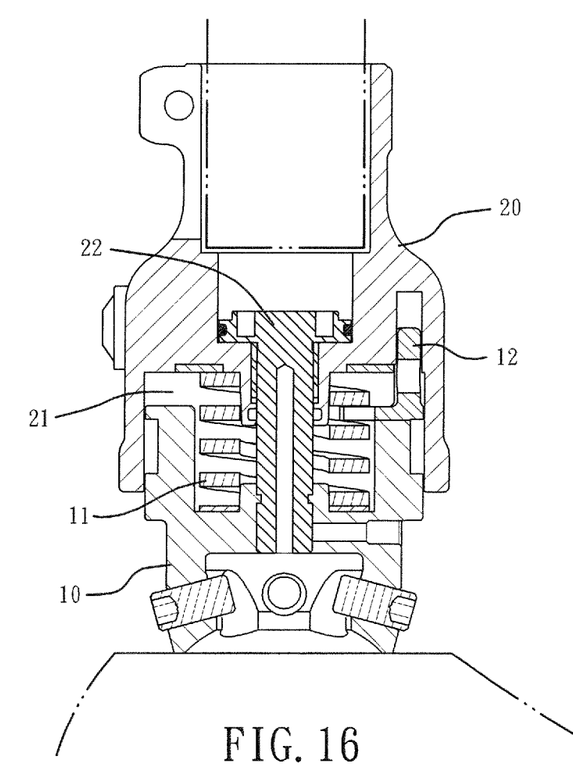
FIG. 16 is a cross-sectional view, taken in a vertical direction, showing said another structure according to the present invention.

Referring to FIGS. 14-16, in an embodiment, the second seat 20 is coupled to an underside of a prosthesis shank and the first seat 10 is coupled to a prosthesis sole. This is provided to suggest that the location where the present invention may be applied is not limited to any specific part, while the structural arrangement is still the same, only the outside configuration being required to modify for adaption.

Figure 17:
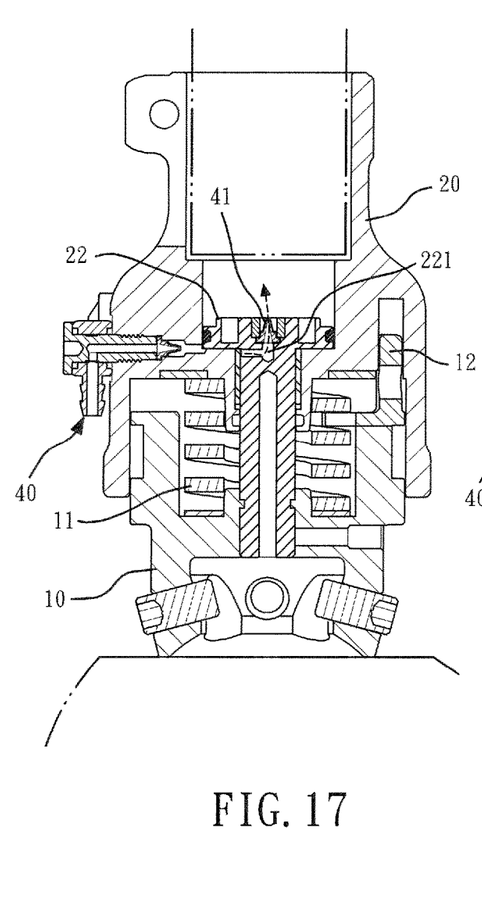
FIGS. 17 and 18 are schematic views illustrating an example of use of said another structure of the present invention to demonstrate an effect of discharge and intake of air.
Figure 18:
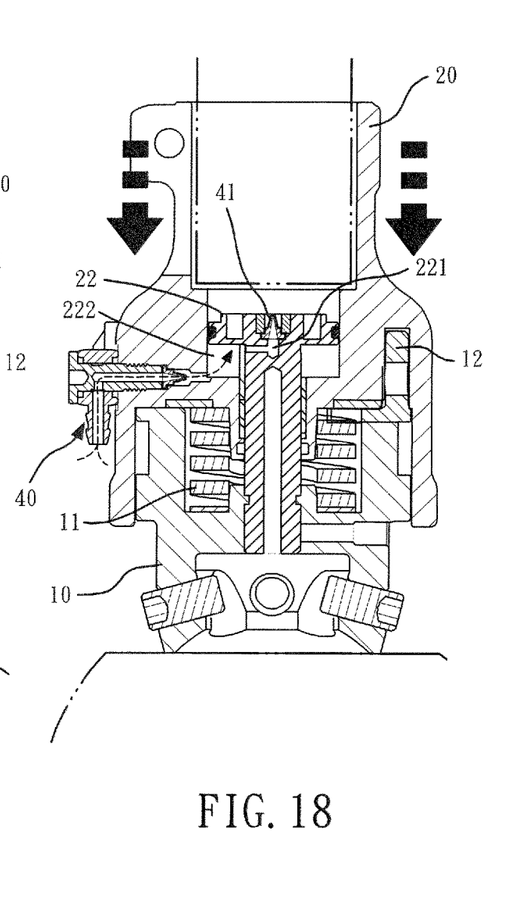

Referring to FIGS. 17 and 18, in order to accommodate the present invention being applied to different location, which may cause the direction in which gas or air is discharged from the present invention, the main axle 22 is formed with an air passage 221 in such a way that one end of the air passage 221 is set in communication with the outside of the second seat 20 and an opposite end of the air passage 221 is set in communication with an air compartment 222 formed and delimited by an outside surface on an upper side of the main axle 22 and an inside surface of the second seat 20. The second seat 20 is provided with a one-way valve 40, and the one-way valve 40 allows external gas or air to flow, in one single direction, into the air compartment 222. The air passage 221 is connected, at one end thereof, to a reverse stop valve 41, and the reverse stop valve 41 allows gas or air to flow from the air passage 221, in one single direction, to the outside of the second first seat 20.

As such, when the second seat 20 moves upward, the air compartment 222 is compressed and gas or air discharges through the air passage 221 and the reverse stop valve 41.

Oppositely, when the second seat 20 moves downward, an effect of intake is caused and external gas or air is drawn through the one-way valve 40 into the air compartment 222.

We claim:

1. A shock-absorbing twisting structure, comprising:
   a first seat, which comprises an elastic member, a stop member being arranged at one side of the first seat; and
   a second seat, which is formed with a receiving chamber that is fit over the first seat, such that the elastic member is set in elastic engagement with and is supported between the first seat and the second seat, a main axle penetrating through the second seat and received in the first seat to set the second seat in a rotatable condition, an elastic unit being arranged at each of two sides of the receiving chamber and the stop member.

2. The shock-absorbing twisting structure according to claim 1, wherein the second seat is provided on an upper side thereof with a pivot axle, the pivot axle being adapted to pivotally connect with an arc plate of a knee joint, the main axle being provided thereon with an elastic element, the elastic element extending through a bottom of the knee joint, the second seat being coupled to an underside of the knee joint, the first seat being adapted to couple to a prosthesis shank.

3. The shock-absorbing twisting structure according to claim 1, wherein the elastic unit comprises an adjusting member, an elastic body, and a pushing portion, the adjusting member being screwed to the receiving chamber, the elastic body being disposed between the adjusting member and the pushing portion, a transmitting body being arranged between the pushing portion and the stop member to allow the pushing portion to contact and elastically push the transmitting body.

4. The shock-absorbing twisting structure according to claim 1, wherein the main axle comprises an air passage formed therein, the air passage having an end in communication with outside of the first seat, the air passage having an opposite end in communication with an air compartment formed and delimited by an outside surface on an upper side of the main axle and an inside surface of the second seat, the second seat being provided with a one-way valve, the one-way valve allowing external gas to flow, in one single direction, into the air compartment, the air passage being connected at one end thereof to a reverse stop valve, the reverse stop valve allowing gas to flow from the air passage, in one single direction, to outside of the first seat.

5. The shock-absorbing twisting structure according to claim 1, wherein the second seat is adapted to couple to an underside of a prosthesis shank and the first seat is adapted to couple to a prosthesis sole.

6. The shock-absorbing twisting structure according to claim 1, wherein the main axle comprises an air passage, the air passage having one end in communication with outside of the second seat, the air passage having an opposite end in communication with an air compartment formed and delimited by an outside surface on an upper side of the main axle and an inside surface of the second seat, the second seat being provided with a one-way valve, the one-way valve allowing gas to flow, in one single direction, into the air compartment, the air passage being connected, at one end thereof, to a reverse stop valve, the reverse stop valve allowing gas to flow from the air passage, in one single direction, to the outside of the second seat.

* * * * *